(12) United States Patent
Golding et al.

(10) Patent No.: US 7,592,448 B2
(45) Date of Patent: Sep. 22, 2009

(54) MONO AMINE AND DIAMINE DERIVATIVES OF CL-20

(75) Inventors: Peter Golding, Reading (GB); Alistair J Maccuish, Isle of Skye (GB); Anthony John Bellamy, Swindon (GB)

(73) Assignee: The Secretary of State for Defence in Her Britannic Majesty's Government of the United Kingdom of Great Britain and Northern Ireland (GB)

( * ) Notice: Subject to any disclaimer, the term of this patent is extended or adjusted under 35 U.S.C. 154(b) by 535 days.

(21) Appl. No.: 10/547,260

(22) PCT Filed: Mar. 1, 2004

(86) PCT No.: PCT/GB2004/000844

§ 371 (c)(1),
(2), (4) Date: Aug. 29, 2005

(87) PCT Pub. No.: WO2004/076383

PCT Pub. Date: Sep. 10, 2004

(65) Prior Publication Data

US 2006/0157174 A1 Jul. 20, 2006

(30) Foreign Application Priority Data

Feb. 28, 2003 (GB) .................................. 0304555.6

(51) Int. Cl.
*C07D 487/18* (2006.01)
*C07D 487/22* (2006.01)

(52) U.S. Cl. ...................................................... 540/554

(58) Field of Classification Search ................... 540/554
See application file for complete search history.

(56) References Cited

U.S. PATENT DOCUMENTS 6,147,209 A    11/2000   Wardle et al.
6,391,130 B1    5/2002   Sanderson et al.
7,129,348 B1 * 10/2006   Wardle et al. ............... 540/554

FOREIGN PATENT DOCUMENTS

| EP | 0 753 519 B1 | 5/2000 |
| GB | 2 333 292 A | 7/1999 |
| JP | 08 208 655 | 8/1996 |
| WO | WO 96/23792 | 8/1996 |

OTHER PUBLICATIONS

Bazaki, et al., 'Synthesis and Sensitivity of Hexanitrohexaazaisowurtzitane,' *Propellants, Explosives, Pyrotechnics*, 23:333-336 (1998).
Bellamy, et al., 'The Use of the Trifluoroacetyl Protecting Group in the Synthesis of Mono-(4) and Di-Amines (4,10) in the Polynitrohexaazaisowurtzitane Series,' *Propellants, Explosives, Pyrotechnics*, 28(3):157-158 (2003).
Chung, et al., 'New Precursors for Hexanitrohexaazaisowurtzitane,' *J. Heterocyclic Chem.*, 37(6):1647-1649 (2000).
Hamilton, et al., 'Studies of the Synthesis and Crystallization of CL-20,' *Conference on Energetic Materials*, Karlsruhe, Germany, 2000, pp. 21-1 to 21-8.
Patent Abstracts of Japan, vol. 1995, No. 02, & JP 6 321962 A (Asahi Chem. Ind. Co. Ltd.) Abstract (Nov. 22, 1994).
Database WPI. Section Ch. Week 200153, Derwent Publications Ltd., London, GB, XP002285511 & KR 2001 011 940 A (Agency Defense Dev.) (Feb. 15, 2001) Abstract.
Chemical Abstracts No. 133:193114 CA, 'Polynitrohexaazaisowurtzitane derivatives related to hexanitrohexaazaisowurtzitane,' Bellamy, Anthony J., Department of Environmental and Ordnance Systems, Cranfield University, RMCS, Chrivenham, SN6 8LA, UK, International Annual Conference of ICT, Energetic Materials (2000).
Chemical Abstracts No. 133:76150 CA, 'Separation and identification of by-product from nitrolysis of tetraacetytdichloracetylhexaazaisowurtzitane,' Liu, et al., Beijing University of Science and Technology, Beijing, 100081, Peop. Rep. China, 23(2):50-51 (2000).
Chemical Abstracts No. 122:30740 CA, 'Theoretical study of the geometry and heat of formation of the N-nitro derivatives of hexaazaisowurtzitane,' Wang, et al., Dep. Appl. Chem., Chung Cheng Inst. Technol., Ta-His, Taiwan, 9(2):35-43 (1993).
National Defense Industrial Association Strength Through Industry & Technology, 2000 Insensitive Munitions and Energetic Materials Technology Symposium, "IM/EM Technology Implementation in the 21$^{st}$ Century" Proceedings, Event #1550, Hyatt Regency San Antonio, Texas, Nov. 27-30, 2000.

* cited by examiner

*Primary Examiner*—Brenda L Coleman
(74) *Attorney, Agent, or Firm*—Kilpatrick Stockton LLP

(57) ABSTRACT

The invention describes the synthesis of novel mono-amine and di-amine derivatives of hexa-nitro-hexaazaiso-hexawurtzitane (CL-20). The synthesis is affected by the novel use of fluoroacylating compounds to protect the secondary amine groups of acylated precursors to CL-20 against nitrolysis. In so doing the mono-amine and di-amine derivatives of CL-20 are rendered and which in turn may be subsequently utilized as intermediates to generate further novel derivatives with differing physical and chemical properties to the parent compound. Formula (I), wherein: —X=H, and Y=H or $NO_2$.

(I)

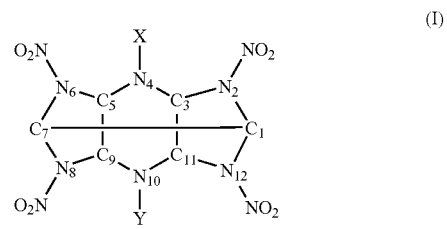

21 Claims, 10 Drawing Sheets

MONO AMINE AND DIAMINE DERIVATIVES OF CL-20

CROSS REFERENCE TO RELATED APPLICATIONS

This application is the U.S. national phase of International Application No. PCT/GB2004/000844 filed on Mar. 1, 2004 and published in English on Sep. 10, 2004 as International Publication No. WO 2004/076383 A1 which application claims priority to Great Britain Application No. 0304555.6.7 filed on Feb. 28, 2003, the contents of which are incorporated by reference herein.

The present invention relates to the synthesis of CL-20 derivatives.

The explosive 2,4,6,8,10,12-hexanitro-2,4,6,8,10,12-hexa aza isowurtzitane, known as CL-20, is an explosive with a high energy density, but is too sensitive for some applications. In its pure form, it is vulnerable to fracture, thus releasing CL-20 powder and dust which can cause accidental explosions.

In order to reduce the likelihood of such an event, crystals of the explosive are coated with a binding agent. The binding agent allows the explosive composition to be worked into a desired shape and decreases its sensitivity. However, the interactions between the explosive and the binding agent are weak, in certain circumstance, in which case the coating will tend to separate from the CL-20 crystals.

A solution is to mix CL-20 with a less sensitive, yet still explosive, compound in order to reduce the sensitivity of the mixture. In such manner CL-20 has been mixed with dinitrotetraoxadiazacyclododecane (TEX) to give a mixture with a lower sensitivity than CL-20 (K. E. Lee et al., "An insensitive alternative to pressed explosive LX-14", pg. 38, National Defense Industrial Association, 2000, Insensitive Munitions and Energetic Materials Technology, Nov. 27-30 2000, San Antonio, Tex.).

Another solution is to seek to modify the chemical structure of CL-20 whilst retaining the nitrohexaazaisowurtzitane residue. This has until hitherto remained an unresolved problem due to the inability to find routes to generating precursor derivatives of CL-20.

The applicant has solved this problem through the chemical synthesis of mono-amine and di-amine derivatives of CL-20 through the use of selective protection against strong nitrolysing reagents by fluoroacylating compounds thereby providing a means for the subsequent generation of further chemically modified derivatives. The applicant describes herein new penta-nitrohexaazaisowurtzitane derivatives and tetra-nitro-hexaazaisowurtzitane derivatives of CL-20. The synthetic route enables selective nitration of a protected polynitrohexazaisowurtzitane residue thereby exposing on deprotection free amine sites for subsequent chemical derivatisation.

Wardle and Hinshaw in UK Patent Application 2333292 A state that the nitration of 2,6,8,12-tetraacetyl-2,4,6,8,10,12-hexa aza iso wurtzitane leads to 2,6,8,12-tetra nitro -2,4,6,8,10,12-hexa aza isowurtzitane. The applicants have been unable to substantiate the claims provided therein and note that the authors of GB 2333292 A provide no experimental details as to how to synthesise this compound. Comparative examples are provided below.

Chung et al. in *J. Heterocyclic Chem.*, vol. 37, 1647, 2000 disclose that the nitration of 2,6,8,10,12-pentaacetyl-2,4,6,8,10,12-hexaazaisowurtzitane according to the method described in GB 2333292 A leads to the generation of CL-20. This is confirmed by the applicant in the comparative examples provided below. The comparative examples provide supporting evidence that the nitration claimed by Wardle and Hinshaw cannot be done. If Wardle and Hinshaw were correct the nitration undertaken as shown in the comparative examples would have given rise to the penta-nitro derivative rather than the hexa-nitro derivative. This was not observed.

H. Bazaki et al. in *Propellants, Explosives, Pyrotechnics* 23, 333-336 (1998) (at p. 333 para 2 and p. 334, para. 3.1) disclose that the preparation of AC-HNIW using a nitrating agent and a precursor synthesised from hexabenzyl hexaazaisowurtzitane (synthesised according to the a method in JP 08,208,655) manufacture yields PNIW a mono-amino-pentanitro-hexa azaisowurtzitane (the mono-amine derivative referred to herein) as an impurity. The paper however provides no enabling disclosure in terms of the generation and isolation of the compound (PNIW) nor indeed the process for generating it.

Hamilton et al. have suggested the use of nitrolysis of 2,6,8,12-tetraacetyl-2,4,6,8,10,12-hexaazaisowurtzitane to form the di-amine derivative 2,6,8,12-tetranitro-2,4,6,8,10,12-hexaazaisowurtzitane (ICT Conference on Energetic Materials, Karlsruhe, Germany, 2000, 21-1 to 21-8). The applicants however have been unable to generate the di-amine derivative according to their suggested route. Comparative examples are provided below.

Wang and Chen have provided a theoretical study only of the heat of formation of the N-nitro derivatives of hexaazaisowurtzitane *Huoyao Jishu* (1993), 9(2), 35-43.

Therefore to the knowledge of the applicant there has been no prior synthesis of the mono-amine and diamine derivatives stated herein.

Accordingly compounds of formula (I) are provided:

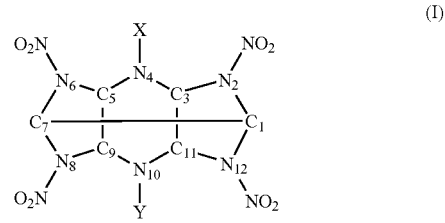

wherein:
X=H, and
Y=H or $NO_2$

The compounds of formula (I) are explosives per se or can be used as precursors and/or intermediates to the preparation of explosives and compositions thereof. Impact sensitivity studies (Rotter Impact Test, 5 Kg) indicate that the mono-amine derivative has a Figure of Insensitiveness value of approx. 16 and the di-amine has a value of approx. 12.

It is the introduction of the free amine groups at either one or both of the n-4 and n-10 positions on the poly-nitrohexaazaisowurtzitane residue that enables the residue to be subsequently modified using relatively straight forward chemistry in order to generate derivatives of CL-20 with different chemical and physical properties to the parent molecule.

In order to demonstrate that derivatives may be synthesised from compounds of formula (I) by reactivity at the n-4 and n-10 sites specific examples are provided below. The structural possibilities are of course extremely extensive although the applicant has ascertained that the extend of derivatisation chemistry is in fact more limited than might have been expected by the skilled man.

Poly-nitro derivatives synthesised from compounds of formula (I), will be energy rich on account of the high stoichiometric ratio of nitro groups within the compound. These derivatives may not however be explosive materials in their own right but will have modified chemical and physical properties in comparison to CL-20 from which they are derived.

In a further application and building upon the concept of the energetic nature of the derivatives. It is clear that the derivatives may be chemically combined with inert binding agents such as hydroxyl terminated polybutadiene (HTPB) or energetic binding agents such as poly-(3-nitratomethyl-3-methyloxetane) known as poly-NIMMO to form new explosive compositions. Again these new compositions will have modified explosive behaviour in comparison to CL-20 per se.

A synthetic route to compounds of formula (I) starting from compounds of formula (II) is provided:
wherein formula (II) comprises:

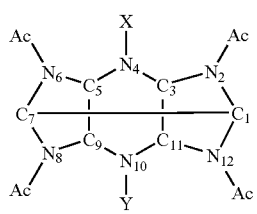

(II)

X=Y=H or,
X=Ac and Y=H
Ac =COCH$_3$, COCH$_2$R where R=C$_1$-C$_{10}$, alkyl (linear branched), —CH$_2$—C$_6$H$_5$, C$_1$-C$_{10}$ arylalkyl).
and wherein the synthetic route comprises the sequential steps of:
(1) fluoroacylation to protect the non-acylated secondary amine group(s) at the n-4 and/or n-10 positions, followed by
(2) nitrolysis of the product of step (1), followed by (3) deprotection by solvolysis of the product of step (2).

The synthesis of the starting material of formula (II) may be found in WO9623792 and EP 0753519.

Step (1) is performed by reacting at least one of the non-acetylated secondary amine groups (at positions n-4 and n-10) with a fluoroacylating reagent. In a specific embodiment the fluorinated acyl reagent may be a tri-fluoroacylating compound such as trifluoroacetic anhydride or a mixture of trifluoroacetic acid and trifluoroacetic anhydride or a pentafluorinated anhydride such as pentafluoropropionic anhydride or CF$_3$COCl.

The trifluoroacetyl group when used as a protecting group for the nitrogen atoms at the n-4 and n-10 positions provides excellent protection against nitrolysis for hexa aza isowurtzitane compounds. Indeed the use of trifluoroacylation as a means of generating a protecting group to the nitrogen atom of the free amine groups enables the synthesis of the formula (I) compounds to be derived by this route.

It is found that fluoroacylation may be achieved in an unselective manner or a selective manner according to the choice of fluoroacylating reagent. This in turn may be used to select the amine stoichiometry of the ultimate end product. Trifluoroacetic acid has been found to fully fluoroacylate the di-amine derivate of formula (II) whereas a mixture of trifluoroacetic acid and trifluoroacetic anhydride has been found to selectively fluoracetylate at only one of the n-4 or n-10 secondary amines.

Step (2) is performed by the nitrolysis of the product of step (1) using concentrated nitric and concentrated sulphuric acids or other nitrolysing agents such as nitric acid/oleum. The skilled man will appreciate that other well known nitrolysing reagents such as but not limited to N$_2$O$_5$ (dinitrogen pentoxide) as well as NOBF$_4$ and NO$_2$BF$_4$ would equally effectively carry out this nitrolysis.

Step (3) is performed by solvolysis of the compound formed in step (2) using an alcohol such as ethanol (and optionally sodium acetate) however solvolysis could equally be achieved through use of any alcohol such as methanol or propanol as well as water. The skilled man will appreciate that solvolysis could also be achieved by using any combination of a carboxylic acid salt with an alcohol such as for example sodium propionate in ethanol.

In industrial practice it may be commercially desirable to commence synthesis of either the mono-amine derivative or the di-amine derivative from a single starting material. In the case where a compounds of formula I having X=Y=H is the starting material, a means of generating either the tetra-nitro derivative or the penta-nitro derivative may be occasioned by complete or selective solvolysis respectively.

In order to bring about complete solvolysis of the tetra-nitro derivative sodium acetate (or other carboxylic acid salt) is required to effect solvolysis (i.e. stronger conditions are required). Solvolysis of the penta-nitro derivative does not require sodium acetate (or other carboxylic acid salt). If it is desired to effect selective solvolysis of the tetra nitro derivative then only ethanol or other alcohol should be used.

Further, in the case where X=Y=H the above three step synthetic pathway leads to the formation of either the tetra-nitro-hexaazaisowurtzitane derivative (tetra-nitro derivative) or the penta-nitro derivative according to the strength of the acylating reagent. The use of a strong fluoroacylating reagent such as trifluoroacetic anhydride will fully acylate the di-amine starting material whereas use of a weaker fluoroacylating reagent such as trifluoroacetic acid and trifluoroacetic anhydride will only partially acylate the di-amine to produce the mono-amine. In the case of the former, subsequent nitrolysation and solvolysis will generate the penta-nitro derivative whereas in the case of the latter the tetra-nitro derivative will be generated.

Again, and in the case where in formula (I) X=Y=H, an alternative means of generating the penta-nitro derivative is to introduce a further acylation step into the synthetic pathway prior to step (1). In this manner the di-amine starting product is converted to the mono-amine acetylated intermediate (i.e. X=H, Y=Ac).

Accordingly there is provided a further acylation step prior to step (1) to form the acylated derivative wherein the tetra-acylated di-amine starting material is acylated to form a penta-acylated mono-amine intermediate.

The acylation step may be conveniently performed by reacting the compound of formula I having X=Y=H with an acetylating reagent such as acetic anhydride and acetic acid (AcOH/Ac$_2$O). The skilled man will appreciate that other common acylation agents such as acyl anhydrides, acid anhydrides and acid chlorides,could equally be used to effect this reaction.

An alternative means of generating the penta-nitro derivative where in formula (I) both X=Y=H, is to introduce a further solvolysis step (step 5) followed by a further nitrolysis step (step 6) between steps (2) and (3).

Accordingly there is provided a further two steps to the reaction synthesis, wherein after step (2) but prior to step (3) the following two sequential steps are introduced:
(5) the product of step (2) is selectively deprotected by solvolysis, followed by
(6) nitrolysis of the product of step (5).

Selective deprotection at Step (5) may be achieved through the use of ethanol however selective deprotection by solvolysis could equally be achieved through the use of any alcohol such as methanol or propanol as well as water.

Step (6) may be achieved through the use of concentrated nitric and sulphuric acids or other nitrolysing agents such as nitric acid/oleum. The skilled man will appreciate that other nitrolysing reagents such as $N_2O_5$ or $NOBF_4$ and $NO_2BF_4$ would equally effectively carry out this nitrolysis.

The compounds of formula (I) may be used as intermediates or precursors for the production of compounds derived from the poly-nitro-hexaazaisowurtzitane residue. The free amine groups at the n-4 and/or n-10 positions enables these amine sites to participate in substitution and addition reactions with other reagents.

Such derived compounds may be explosive in their own right or non-explosive but in most instances they will be sufficiently energetic to be incorporated into materials of use as explosives.

The applicants that the possibility of deriving products from formula (I) is more limited in scope than might at first be expected as these compounds are less reactive than might at first have been expected. For example the mono-amine and di-amine derivatives have been found not to react with alkyl halides or phenyl halides such as benyl bromide. Moreover, acetylation has required the presence of sulphuric acid.

Accordingly compounds of formula (III) are provided:

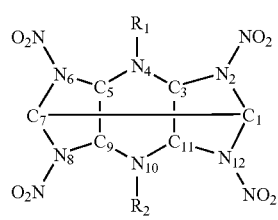

(III)

wherein:

$R_1$ and $R_2$ are independently selected from:

$C_1$-$C_{10}$ alkyl, $C_1$-$C_{10}$ alkylaryl, $CH_2$—$C_6H_5$, $C_1$-$C_{10}$ polyethers, $C_1$-$C_{10}$ fluorinated polyethers, $C_1$-$C_{10}$ fluorinated alkyl, $CH_2$—$C_6F_5$, COR' where R'=$C_1$-$C_{10}$ alkyl, $COCl_3$, $COCCl_3$ CONHR", where R"=H, $C_1$-$C_{10}$ alkyl, $COCl_3$, $COCCl_3$ $C(O)C_mF_{2m}C_pH_{2p+1}$, wherein m and p are integers and are independently chosen from the range 1 to 19 and wherein m+p is less than or equal to 20

$COCF_3$

A synthetic route to compounds of formula (III) starting from compounds of formula (I) is provided comprising reacting a compound of formula (I) with an acyl halide (such as for example an acyl bromide or an acyl chloride).

The acyl halide may comprise $C_1$-$C_{10}$ alkylacyl halides, $C_1$-$C_{10}$ alkylaryl acyl halides, $CH_2$-arylacyl halide, and R-acyl halides where R comprises $C_1$-$C_{10}$ polyethers, $C_1$-$C_{10}$ fluorinated polyethers, $C_1$-$C_{10}$ fluorinated alkyl, $CH_2$-fluorinated phenyl, COR' where R'=$C_1$-$C_{10}$ alkyl, $COCl_3$, $COCCl_3$ CONHR", where R"=H, $C_1$-$C_{10}$ alkyl, $COCl_3$, $COCCl_3$ $C(O)C_mF_{2m}C_pH_{2p+1}$, wherein m and p are integers and are independently chosen from the range 1 to 19 and wherein m+p is less than or equal to 20 and $COCF_3$.

In a specific embodiment the alkylacyl halide may be acetyl chloride.

A synthetic route to compounds of formula (III) starting from compounds of formula (I) is provided comprising reacting a compound of formula (I) with an acyl anhydride.

The acyl anhydride may comprise $C_1$-$C_{10}$ alkylacylanhydride, $C_1$-$C_{10}$ alkylarylacylanhydride, $CH_2$-arylacylanhydride, and R-acylanhydrides where R comprises $C_1$-$C_{10}$ polyethers, $C_1$-$C_{10}$ fluorinated polyethers, $C_1$-$C_{10}$ fluorinated alkyl, $CH_2$-fluorinated phenyl, as well as R acyl anhydrides where R comprises:

COR' where R'=$C_1$-$C_{10}$ alkyl, $COCl_3$, $COCCl_3$

CONHR", where R"=H, $C_1$-$C_{10}$ alkyl, $COCl_3$, $COCCl_3$ $C(O)C_mF_{2m}C_pH_{2p+1}$, wherein m and p are integers and are independently chosen from the range 1 to 19 and wherein m+p is less than or equal to 20 and $COCF_3$.

In a specific embodiment the acyl anhydride may be acetic anhydride.

A further synthetic route to compounds of formula (III) starting from compounds of formula (I) is provided comprising reacting the compounds of formula (I) with an isocyanate.

In a specific embodiment the isocyanate may be N-(chlorocarbonyl)isocyanate or trichloroacetyl isocyanate.

In a further embodiment after reacting a compound of formula (III) with an isocyanate the product may be further reacted with a chlorocarbonyl acetate and an alcohol to form a urethane derivative of hexaazaisowurtzitane.

In a specific embodiment alcohol may be methanol or ethanol.

The invention will now be described by way of example and with reference to the following figures of which:

SYNTHESIS OF COMPOUNDS OF FORMULA (I)

Reaction Scheme 1

Figure 1:
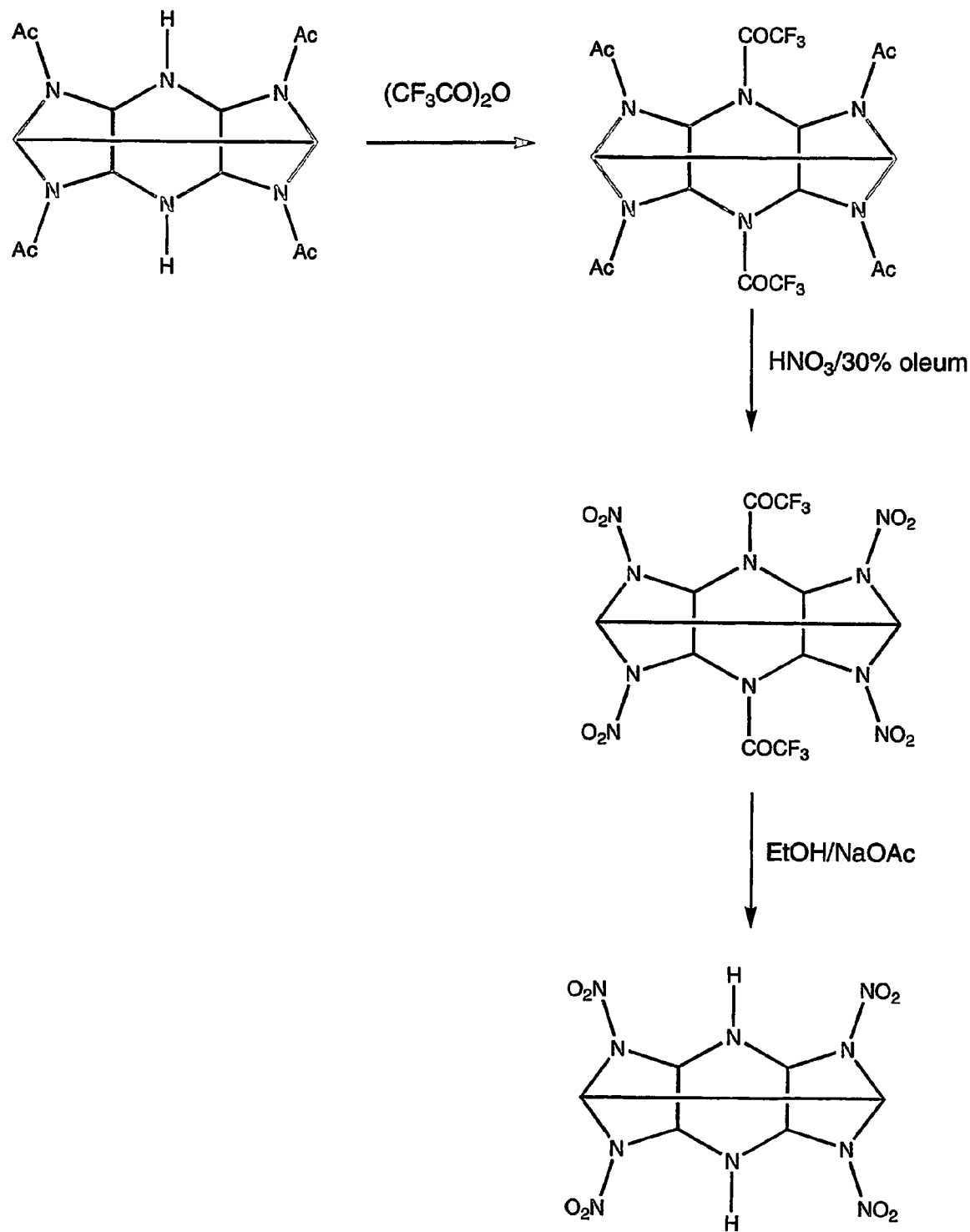
FIG. 1 shows a synthetic route in accordance with the present invention for the production of 2,6,8,12-tetranitro-2,4,6,8,10,12-hexaazaisowurtzitane. This synthetic route is entitled reaction scheme 1.

(a) Synthesis of 2,6,8,12-tetra nitro-2,4,6,8,10,12-hexa aza isowurtzitane

The reaction comprises three steps:

(1) the preparation of 2,6,8,12-tetraacetyl-4,10-bis(trifluoroacetyl)-2,4,6,8,10,12-hexaazaiso wurtzitane (B) from 2,6,8,12-tetraacetyl-2,4,6,8,10,12-hexaazaisowurtzitane (A), (2) the nitration of 2,6,8,12-tetraacetyl-4,10-bis(trifluoroacetyl)-2,4,6,8,10,12-hexaazaiso wurtzitane (B) to form 2,6,8,12-tetranitro-4,10-bis(trifluoroacetyl)-2,4,6,8,10,12-hexaazaisowurtzitane (C) and (3) the removal of the two trifluoroacetyl groups from 2,6,8,12-tetranitro-4,10-bis(trifluoroacetyl)-2,4,6,8,10,12-hexaazaisowurtzitane (C) to form 2,6,8,12-tetranitro-2,4,6,8,10,12-hexaazaisowurtzitane (D).

(1) Preparation of 2,6,8,12-tetraacetyl-4,10-bis (trifluoroacetyl)-2,4,6,8,10,12-hexaazaisowurtzitane (B)

Compound A (6.0 g) was suspended in trifluoroacetic anhydride (30 ml) and stirred at 38° C. for 48 hours. An aliquot removed and analysed after 24 hours indicated that the reaction was complete at that stage. Excess anhydride was removed on a rotary evaporator to leave a pink-white solid. The solid was dissolved in chloroform and evaporated to dryness, this process then being repeated. The resulting solid was dried under vacuum at 50° C. for 8 hours, giving 9.62 g, 102% crude yield.

NMR and IR analysis indicated that the resulting solid was compound (B).

$^1$H NMR (DMSO-d6): δ2.06 (broad s, 12.4H, 4×COCH$_3$), 6.63-7.00 ppm (m, 6.0H, 6×CH).

$^{19}$F NMR: δ 66.52 and 66.88 ppm.

(2) Preparation of 2,6,8,12-tetranitro-4,10-bis (tri fluoro acetyl)-2,4,6,8,10,12-hexaazaiso wurtzitane (C)

A nitrating acid was prepared by the dropwise addition of 30% SO$_3$ fuming sulphuric acid (5.0 ml) to 99.5% nitric acid (30.0 ml). An ice/water bath was used to keep the temperature of the reaction mixture below 15° C. during the addition process. The mixed acid was then cooled to 5° C. before the rapid addition with vigorous stirring of crude compound B (7.0 g) via a solids funnel. When all of compound B had dissolved, the solution was heated to 50° C. for 4 hours. TLC analysis of a sample at this point indicated the presence of uncer-nitrated products, so heating was continued at 60° C. for a further 1.5 hours. The solution was removed from the heat and drowned in 500 ml of an ice/water mixture. The precipitate that formed was removed by filtration, washed with water until washings were neutral, then dried overnight in a vacuum dessicator to leave a fine white solid (6.59 g, 92% crude yield).

NMR and IR analysis indicated that the resulting solid was compound C.

$^1$H NMR (DMSO-d6): δ7.31-7.41 (m, 3.6H, 4×CH), 8.01 ppm (s, 2.0H, 2×CH)

$^{19}$F NMR: δ 67.24 to 66.7 ppm (m).

(3) Preparation of 2,6,8,12-tetranitro-2,4,6,8,10,12-hexa aza isowurtzitane (D) Crude compound (C) (0.8 g) was added to a pre-prepared solution of sodium acetate (140 mg) in dry ethanol (14 ml). A precipitate formed immediately after the crude compound (C) had dissolved, and a yellow colouration was observed in the mixture. Stirring was continued for a further 10 minutes, then the precipitate was filtered off, washed with water and dried in a vacuum dessicator overnight to leave a white solid (303 mg, 58.7% yield)

NMR and IR analysis indicated that the resulting solid was compound (D). DSC (10 K/min) indicated onset of decomposition at 183° C. There was no explosive exotherm using these DSC conditions. This indicates that compound (D) is a thermally stable explosive, relative to CL-20.

$^1$H NMR (DMSO-d6): δ5.44 (s, 1.9H, 2×NH), 6.28 (s, 4.1H, 4×CH), 7.57 ppm (s, 2.0H, 2×CH).

$^{13}$C NMR (acetone-d6): δ72.48, 72.98 ppm.

1H-13C correlation: 5.44 ppm (H-4,H-10) uncoupled, 6.28 (H-3, H-5, H-7, H-9) coupled to 72.48 9C-3, C-5, C-7, C-9), 7.57 ppm 9H-1,H-11) coupled to 72.98 (C-1, C-11).

Reaction Scheme 2

(b) Synthesis of 2,6,8,10,12-pentanitro-2,4,6,8,10,12-hexa aza iso wurtzitane

The reaction comprises four steps:

(1) the preparation of 2,6,8,10,12-pentaacetyl-2,4,6,8,10,12-hexaazaisowurtzitane (E) from 2,6,8,12-tetraacetyl-2,4,6,8,10,12-hexaazaisowurtzitane (A);

(2) the preparation of 2,6,8,10,12-pentaacetyl-4-trifluoroacetyl-2,4,6,8,10,12-hexaazaiso wurtzitane (F) from 2,6,8,10,12-pentaacetyl-2,4,6,8,10,12-hexaazaisowurtzitane (E);

(3) the nitration of 2,6,8,10,12-pentaacetyl-4-trifluoroacetyl-2,4,6,8,10,12-hexaazaiso wurtzitane (F) to form 2,6,8,10,12-pentanitro-4-trifluoroacetyl-2,4,6,8,10,12-hexaazaiso wurtzitane (G) and (4) the removal of the trifluoroacetyl group from 2,6,8,10,12-pentanitro-4-trifluoroacetyl-2,4,6,8,10,12-hexa azaisowurtzitane (G) to form 2,6,8,10,12-pentanitro-2,4,6,8,10,12-hexaazaisowurtzitane (H).

(1) Preparation of 2,6,8,10,12-pentaacetyl-2,4,6,8,10,12-hexa aza iso wurtzitane from 2,6,8,12-tetraacetyl-2,4,6,8,10,12-hexa azaisowurtzitane A suspension of compound A (1.0 g) in a mixture of glacial acetic acid (15 ml) and acetic anhydride (10 ml) was stirred at 60° C. for 12 hours. Excess acetic acid/anhydride mixture was removed on a rotary evaporator at 60° C. The remaining reaction mixture was dried under vacuum at 60° C. for 6 hours to leave a white solid. This solid was slurried in methanol (200 ml) at 60° C. and filtered hot. The remaining solids in the filter were recovered and extracted in a similar manner with two further portions of hot methanol. The extracts were combined and the methanol was removed on the rotary evaporator and the remaining off-white solid dried under vacuum at 50° C. (6.7 g, 99.5% crude yield, 302-304° C. melting point (DSC, ex methanol).

NMR and IR analysis indicated that the resulting solid was compound (E).

$^1$H NMR (DMSO-d$_6$): δ1.90-2.04 (m, 12.0H, 4×COCH$_3$), 2.18-2.31 (m, 3.1H, COCH$_3$), 4.66-4.85 (m, 0.8H, NH), 5.55-5.58 (m, 1.9H, 2×CH), 6.21-6.77 ppm (m, 4.0H, 4×CH).

(2) Preparation of 2,6,8,10,12-pentaacetyl-4-trifluoroacetyl-2,4,6,8,10,12-hexaazaiso wurtzitane from 2,6,8,10,12-pentaacetyl-2,4,6,8,10,12-hexaazaisowurtzitane.

Crude compound (E) (3.0 g) was stirred in trifluoroacetic anhydride (12 ml) at 38° C. for 48 hours. The resulting clear solution was evaporated to dryness, the resulting solid being redissolved in chloroform and evaporated to dryness twice more. The solid was dried under vacuum at 50° C. to leave a pinkish-white solid (3.3.8 g, 90% crude yield).

NMR and IR analysis indicated that the resulting solid was compound (F).

$^1$H NMR (DMSO-d$_6$): δ1.94-2.09 (m, 12.5H, 4×COCH3), 2.28-2.36 (m, 3.6H, 1×COCH3), 6.45-7.08 ppm (m, 6.0H, 6×CH).

$^{19}$F NMR: δ67.66 and 66.86 ppm.

(3) Preparation of 2,6,8,10,12-pentanitro-4-trifluoroacetyl-2,4,6,8,10,12-hexaazaiso wurtzitane from 2,6,8,10,12-penta acetyl-4-trifluoroacetyl-2,4,6,8,10,12-hexa aza iso wurtzitane A nitrating mixture was formed by the dropwise addition of 30% $SO_3$ fuming sulphuric acid (6.0 ml) to 99.5% nitric acid (13.0 ml). The temperature was kept below 15° C. during the addition by immersion of the reaction vessel in a water/ice bath. The mixed acid was cooled to 5° C. before the rapid addition, with vigorous stirring, of crude compound F (2.0 g) via a solids funnel. When the solid had completely dissolved, the flask was heated at 60° C. for 3 hours. The reaction mixture was allowed to cool before being drowned in an ice/water mixture (200 ml). The flask was washed out with two portions of water (2×50 ml). The dense white precipitate was filtered off, washed with water until the washings were neutral, and dried overnight in a vacuum dessicator (1.2 g, 58% crude yield).

MNR and IR analysis indicated that the resulting solid was compound (G).

$^1$H NMR (DMSO-$d_6$): δ7.54-7.97 (m, 2.0H, 2×CH), 8.12 (s, 1.6H, 2×CH), 8.29 ppm (d, J=7 Hz, 1.4H 2×CH).

$^{19}$F NMR: 67.99 ppm.

TLC analysis of the crude material indicated that CL 20 was a major contaminant. NMR studies indicated that approximately 37% of the crude product was CL-20.

(4) Preparation of 2,6,8,10,12-pentanitro-2,4,6,8,10,12-hexa aza iso wurtzitane (H) from 2,6,8,10,12-pentanitro-4-trifluoroacetyl-2,4,6,8,10,12-hexaazaisowurtzitane (G).

Crude compound (G) (2.0 g) was dissolved in dry ethanol (2 ml) and stirred at room temperature for 48 hours, during which time the solution developed a yellow colouration. The solvent was removed by rotary evaporation and the resulting solid dried under vacuum at 50° C. to leave a yellow solid (1.2 g). TLC analysis of the solid suggested that it consisted of two major components, one of which was CL-20. A portion of the product was resolved by column chromatography, using a 40 cm nylon column of 2 cm diameter packed with silica gel (Merck Kieselgel 60 $F_{254}$), using a 3:2 mixture of n-heptane/ethyl acetate as eluent. After development, the column was cut-up and the products extracted from the silica gel.

MNR and IR analysis indicated that the purified solid was compound (H).

$^1$H NMR (DMSO-$d_6$): δ5.99 (broad s, 0.8H, NH), 6.67-6.72 (m, 2.0H, 2×CH), 7.88 (s, 1.9H, 2×CH), 7.94 ppm (d, J=8 Hz, 2H, 2×CH).

$^{13}$C NMR: 71.19, 73.25, 74.21 ppm.

; $^{H-1}$H correlation (COSY45): 5.99 (H-4) coupled to 6.67-6.72 (H-3, H-5), 6.67-6.72 coupled to 7.94 (H-9, H-11).

$^1$H-$^{13}$C correlation: 6.67-6.72 coupled to 73.25, 7.88 coupled to 74.21 ppm, 7.94 coupled to 71.19.

DSC (10 K/min) of the purified solid recorded the onset of an explosive decomposition exotherm at 168° C., indicating that compound (H) is an explosive compound.

Reaction Scheme 3

(c) Synthesis of 2,6,8,10,12-pentanitro-2,4,6,8,10,12-hexa aza iso wurtzitane

Figure 2:
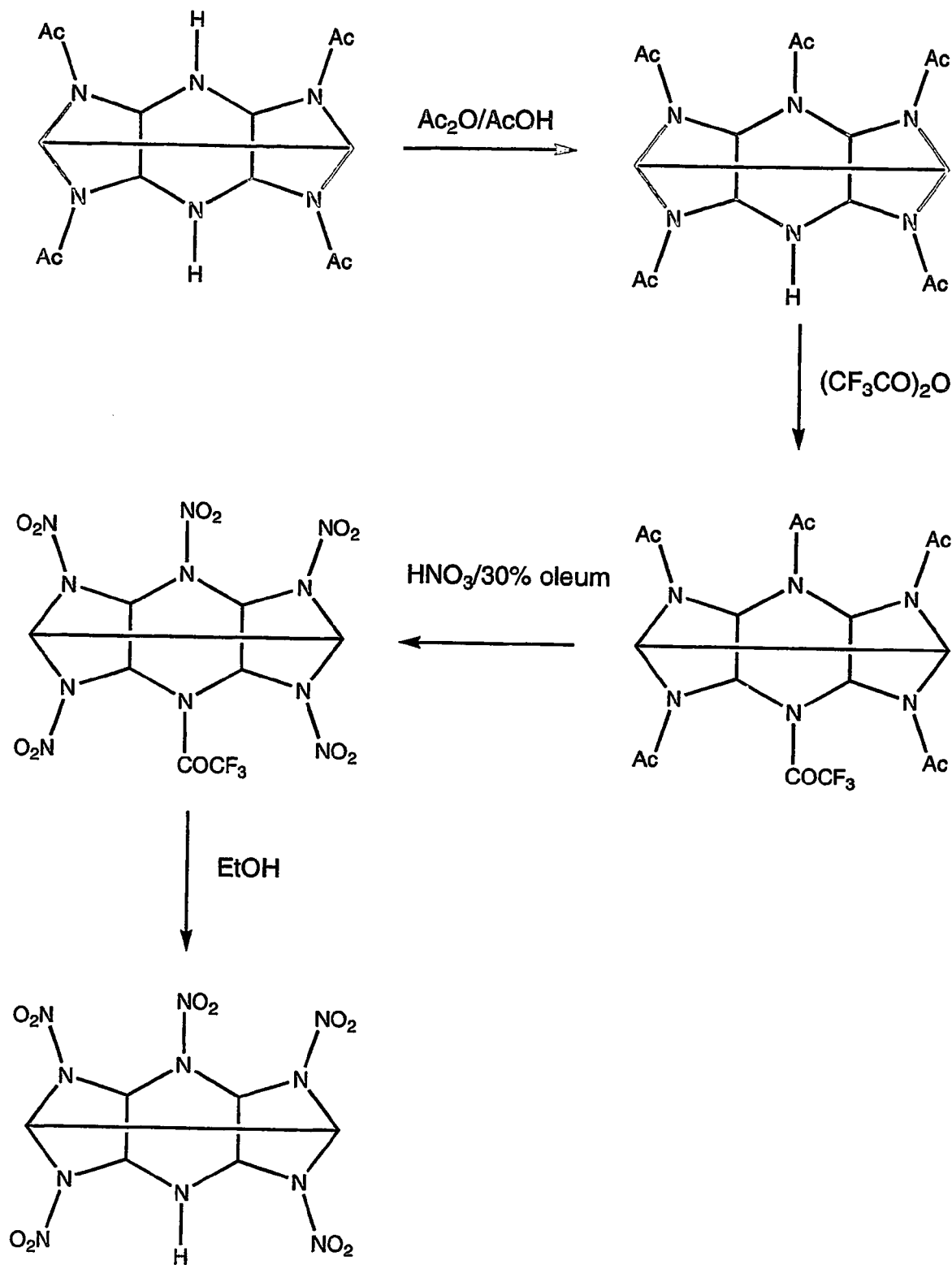
FIG. 2 shows a synthetic route in accordance with the present invention for the production of 2,6,8,10,12-pentanitro-2,4,6,8,10,12-hexaazaisowurtzitane. This synthetic route is entitled reaction scheme 2.
Figure 3:
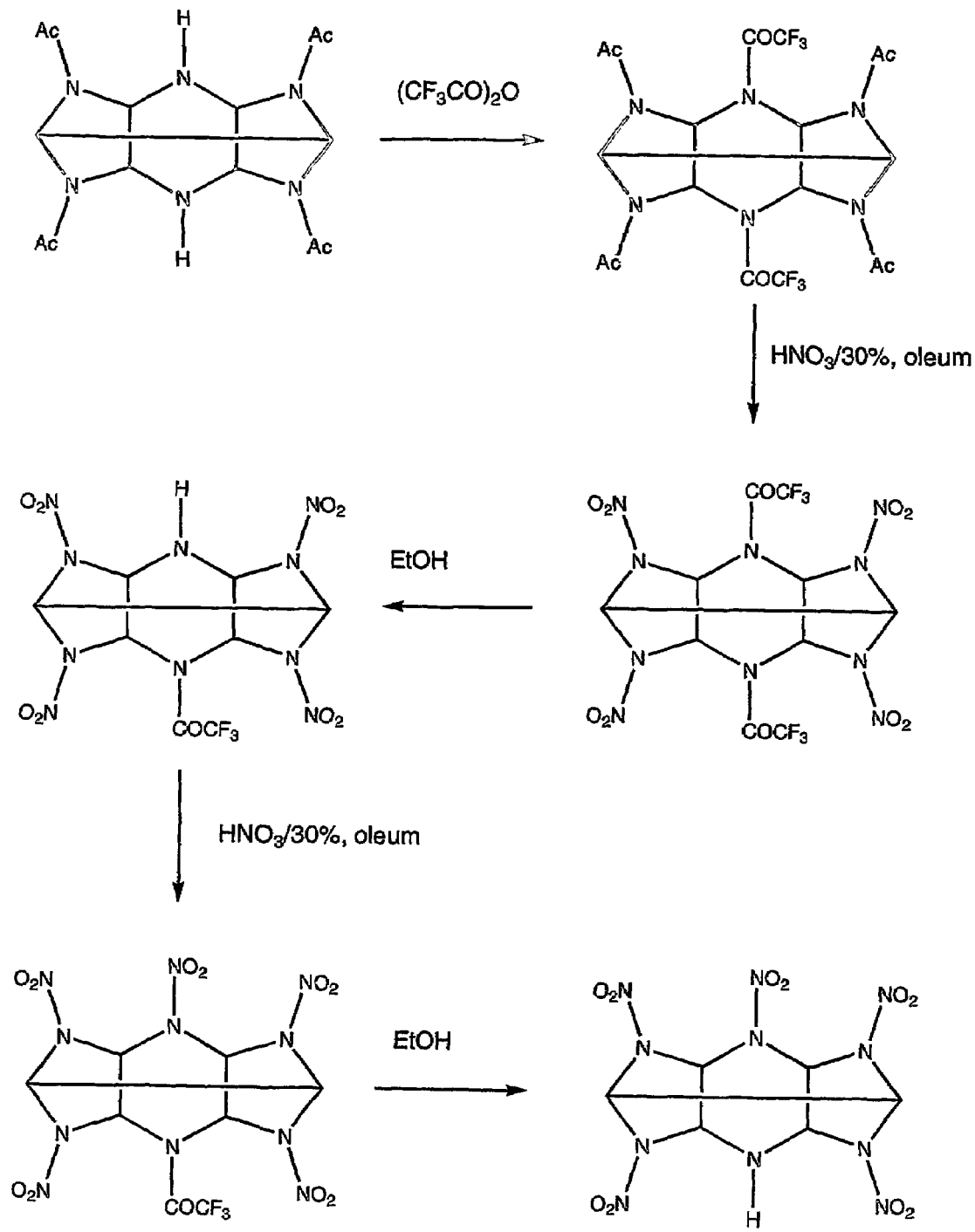
FIG. 3 shows an alternative synthetic route in accordance with the present invention for the production of 2,6,8,10,12-pentanitro 2,4,6,8,10,12-hexaazaisowurtzitane. This synthetic route is entitled reaction scheme 3.
Figure 4:
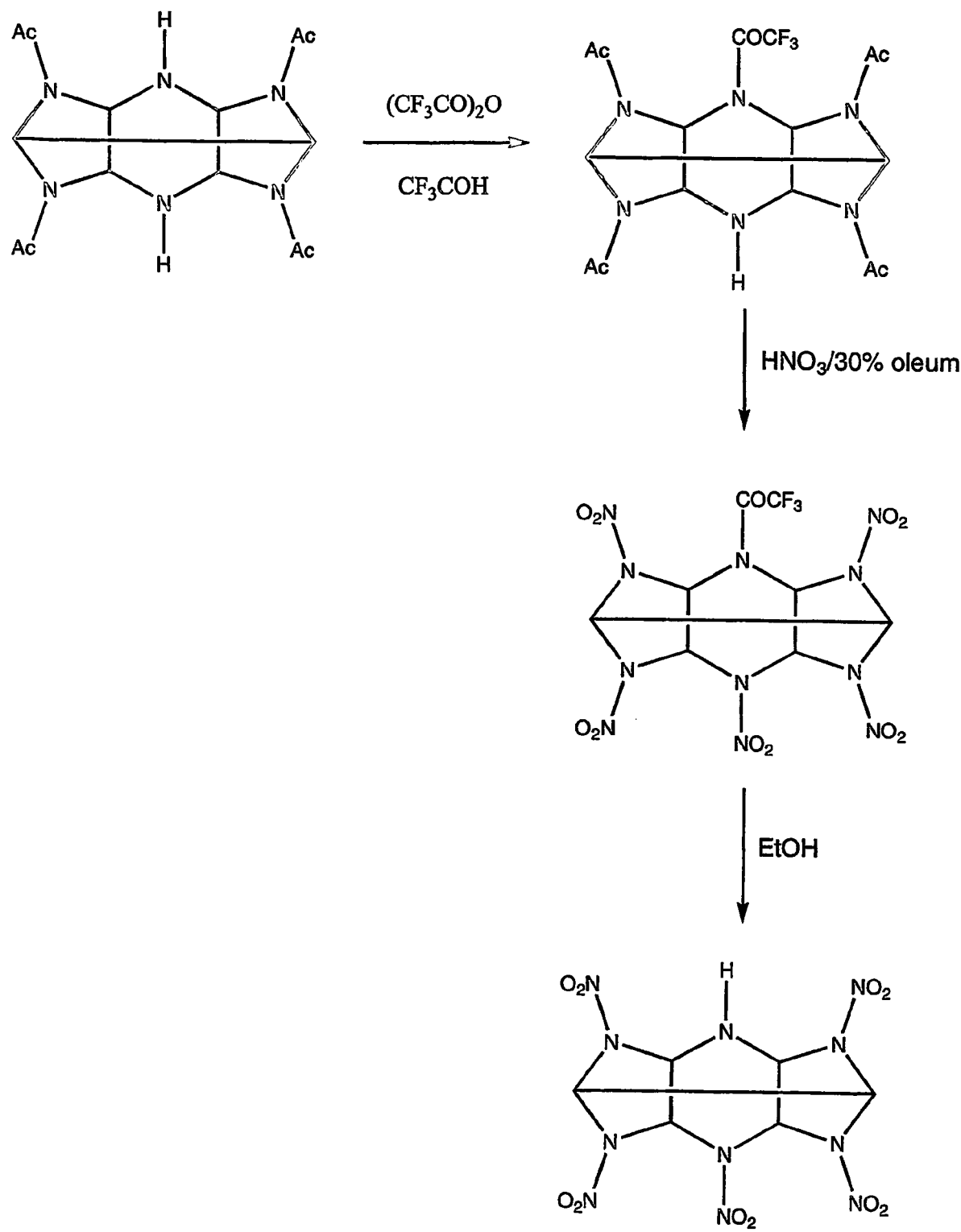
FIG. 4 shows an alternative route synthetic route in accordance with the present invention for the production of 2,6,8,10,12-pentanitro 2,4,6,8,10,12-hexaazaiso wurtzitane. This synthetic route is entitled reaction scheme 4.
Figure 5:
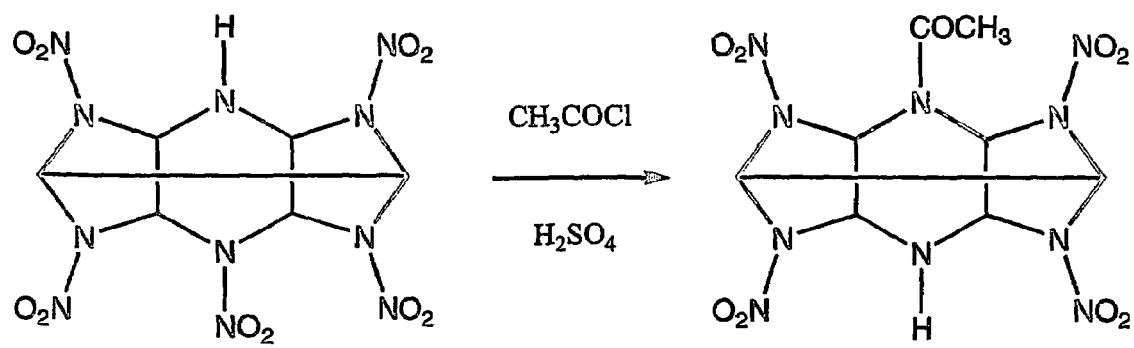
FIG. 5 shows a synthetic route to the acetylation of either the mon-amine or di-amine derivatives using trichloroacetic anhydride. These reactions must be catalysed by the addition of conc. sulphuric acid.
Figure 5:
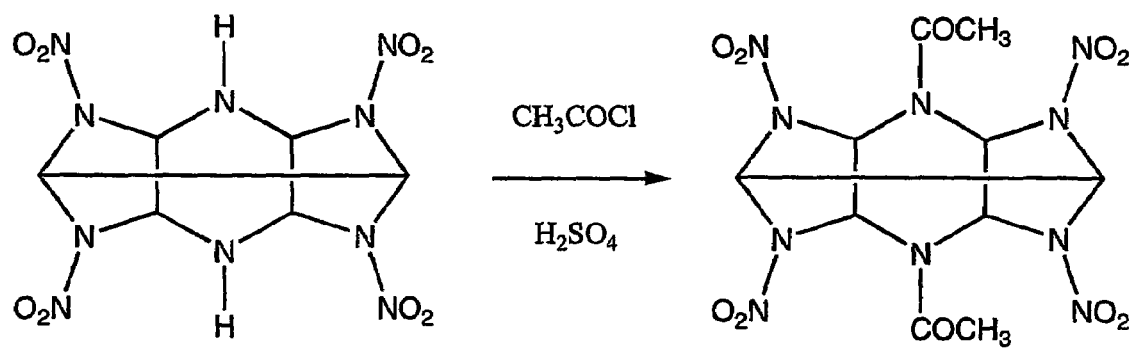
Figure 6:
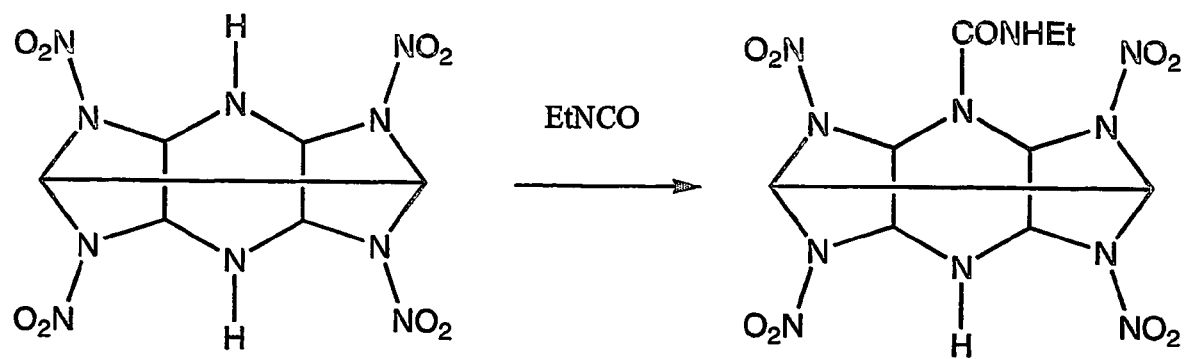
FIG. 6 shows a synthetic route to an amide derivative of CL-20 starting from the di-amine derivative and using an isocyanate as reagent.
Figure 7:
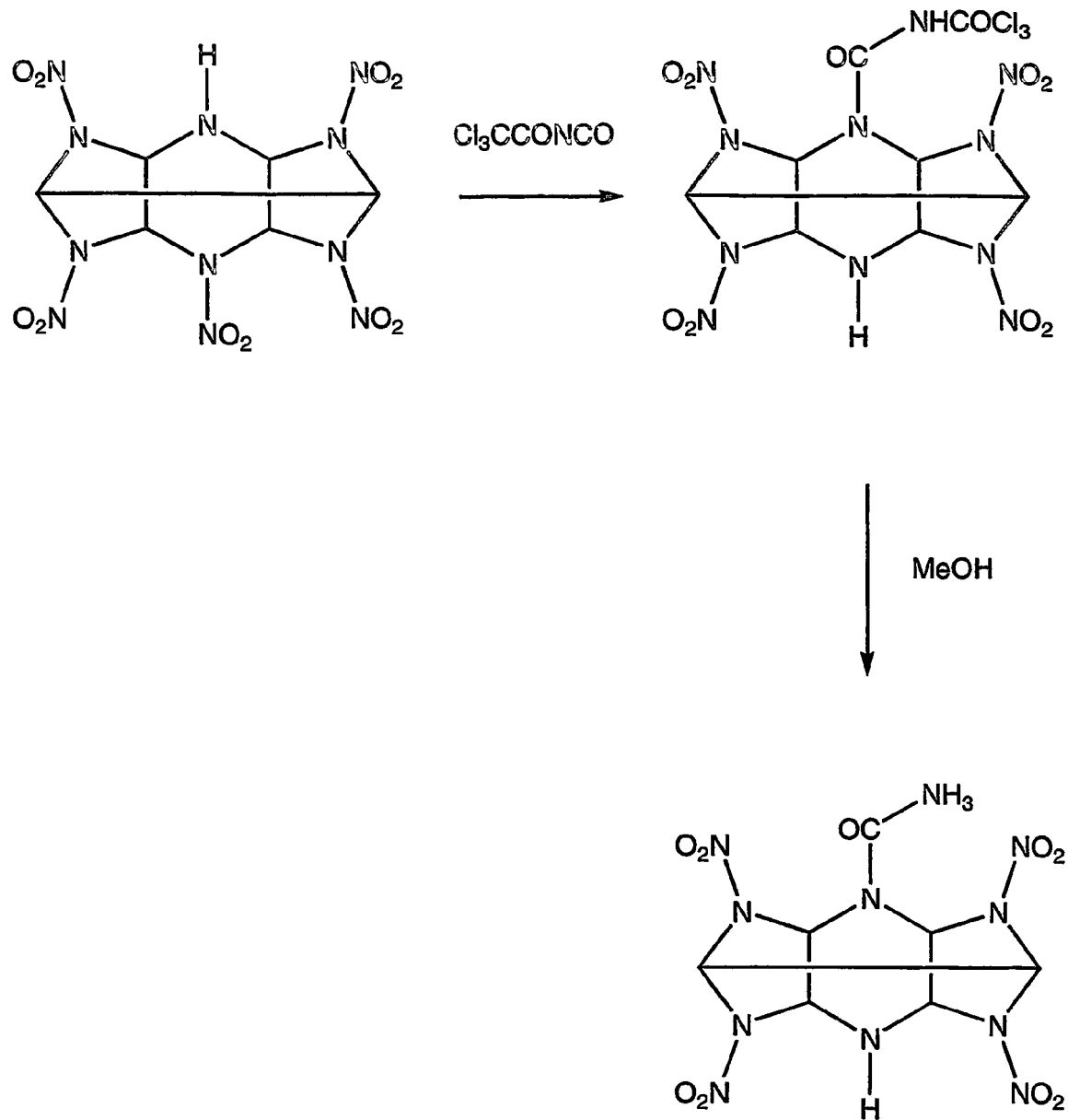
FIG. 7 shows a synthetic route to an amide chloride or an amide (by further methanolysis) starting from the mono-amine derivative and using an isocyanate as reagent.
Figure 8:
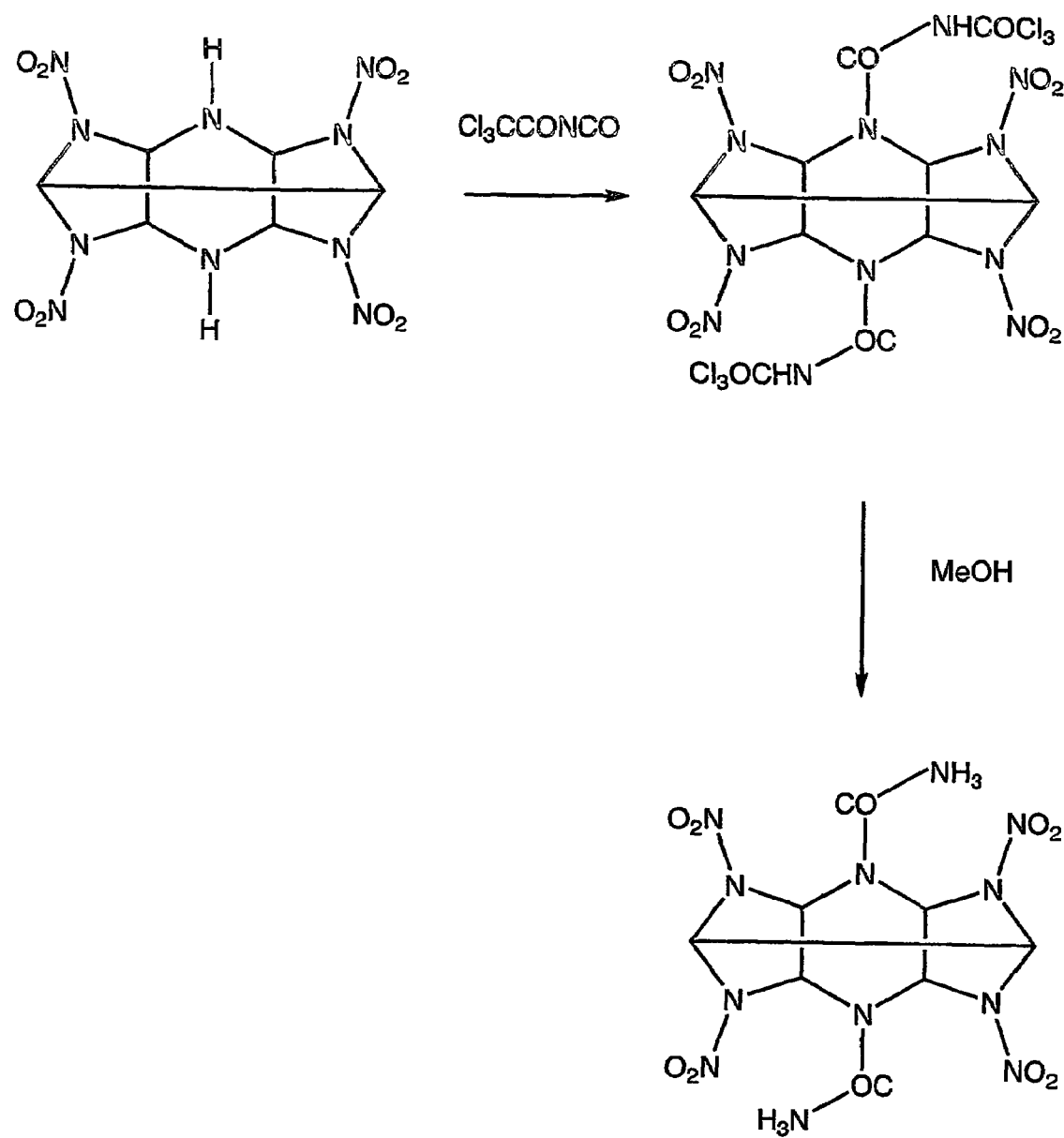
FIG. 8 shows a synthetic route to an amide chloride or an amide (by further methanolysis) starting from the di-amine derivative and using an isocyanate as reagent.
Figure 9:
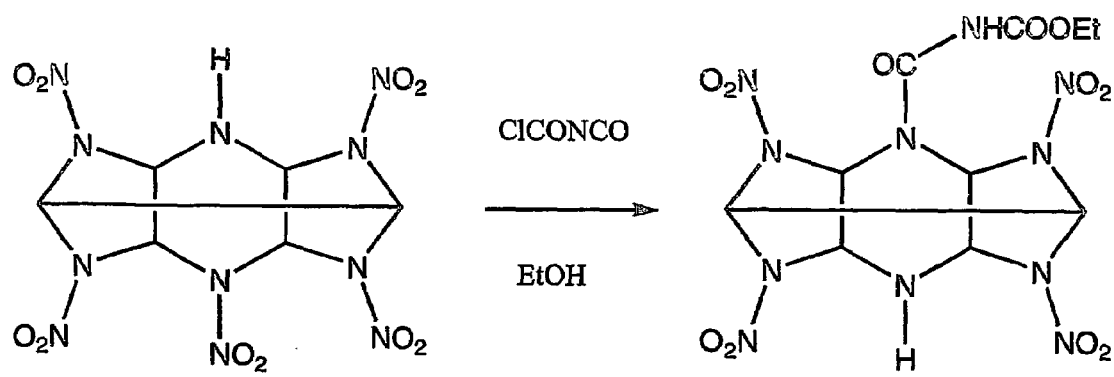
FIG. 9 shows a synthetic route to an amide starting from either the mono-amine or the di-amine and using an isocyanate as reagent to generate the mono-amide or di-amide respectively.
Figure 9:
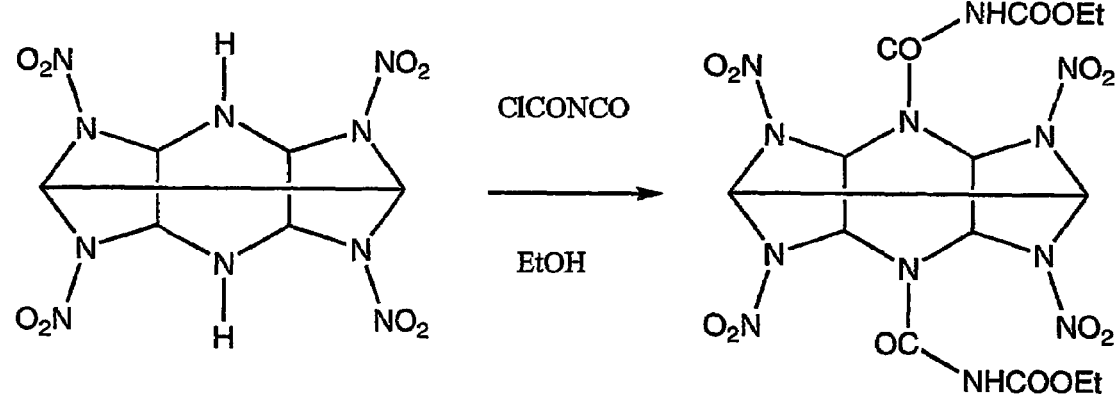
Figure 10:
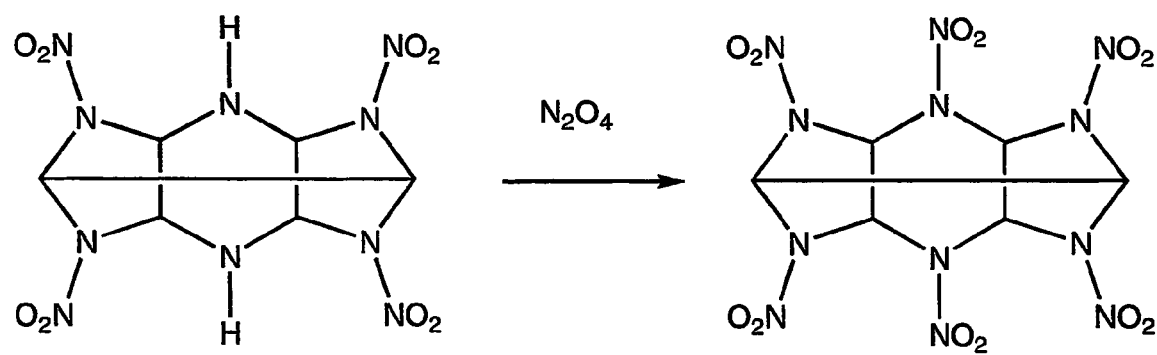
FIG. 10 shows how CL-20 may be generated by nitrolysis of the diamine.

FIG. 3 shows an alternative synthetic route for the production of compound H. It involves more steps than the route of FIG. 2, but is more reagent-efficient. The reaction comprises five steps viz.

(1) the preparation of 2,6,8,12-tetraacetyl-4,10-bis (tri fluoroacetyl)-2,4,6,8,110,12-hexaaziso wurtzitane (B) from 2,6,8,12-tetraacetyl-2,4,6,8,10,12-hexaazaisowurtzitane (A);

(2) the preparation of 2,6,8,12-tetranitro-4,10-(bis) tri fluoroacetyl-2,4,6,8,10,12-hexaazaiso wurtzitane (C) from 2,6,8,12-tetraacetyl-4,10-bis(trifluoroacetyl)-2,4,6,8,10,12-hexaazaiso wurtzitane (B);

(3) the preparation of 2,6,8,12-tetranitro-4-trifluoroacetyl-2,4,6,8,10,12-hexaazaisowurtzitane (J) from 2,6,8,12-tetranitro-4,10-(bis)trifluoroacetyl-2,4,6,8,10,12-hexaazaisowurtzitane (C);

(4) the preparation of 2,6,8,10,12-pentanitro-4-tri fluoro acetyl-2,4,6,8,10,12-hexaazaiso wurtzitane (G) from 2,6,8,12-tetranitro-4-trifluoroacetyl-2,4,6,8,10,12-hexa aza iso wurtzitane (J), and (5) the preparation of 2,6,8,10,12-pentanitro-2,4,6,8,10,12-hexaazaisowurtzitane (H) from 2,6,8,10,12-pentanitro-4-trifluoroacetyl-2,4,6,8,10,12-hexaazaisowurtzitane (G).

Steps (1) and (2) above correspond to steps (1) and (2) of the method described in relation to reaction scheme 1 above.

(3) Preparation of 2,6,8,12-tetranitro-4-trifluoroacetyl-2,4,6,8,10,12-hexaazaiso wurtzitane from 2,6,8,12-tetranitro-4,10-(bis)trifluoroacetyl-2,4,6,8,10,12-hexaazaisowurtzitane.

Compound (C) (2.0 g) was dissolved in dry ethanol (10 ml) and stirred at room temperature for 48 hours. The excess ethanol was removed by rotary evaporation to leave a yellow solid which was dried under vacuum at 50° C. for 6 hours (1.73 g, 105%).

NMR and IR analysis indicated that the solid was compound J.

(2) Preparation of 2,6,8,10,12-pentanitro-4-trifluoroacetyl-2,4,6,8,10,12-hexaazaiso wurtzitane from 2,6,8,12-tetra nitro-4-trifluoroacetyl-2,4,6,8,10,12-hexaazaisowurtzitane.

Compound (J) (1.0 g) was added quickly with vigorous stirring to an ice-cooled mixture of 30% $SO_3$ fuming sulphuric acid (0.2 ml) and 99.5% nitric acid (3.0 ml). The mixture was allowed to warm slowly to room temperature and then stirred for 4 hours. The reaction mixture was then drowned in an ice/water mixture (100 ml) and the white precipitate which formed was removed by filtration and washed with several large portions of water before being dried overnight in a vacuum dessicator (0.96 g, crude yield 87%).

NMR and IR analysis indicated that the solid was compound (G).

$^1$H NMR ($d_6$-acetone): 7.70-7.87 (m, 2.6H, 2×CH), 8.15 (s, 2.1H, 2×CH), 8.26 ppm (d, J=7 Hz, 2.0H, 2×CH)

$^{13}$C NMR ($d_6$-acetone): 71.21, 73.26, 74.22 ppm.

$^{19}$F NMR ($d_6$-acetone): 68.41 ppm.

(3) Preparation of 2,6,8,10,12-pentanitro-2,4,6,8,10,12-hexa azaisowurtzitane from 2,6,8,10,12-pentanitro-4-trifluoro acetyl-2,4,6,8,10,12-hexaazaisowurtzitane.

Compound (G) (0.50 g) was dissolved in dry ethanol (10.0 ml) and stirred at room temperature for 48 hours. The solution was then evaporated to dryness and the resulting yellowish solid was dried under vacuum at 50° C. for 6 hours (0.45 g).

NMR analysis of the solid indicated that the solid was predominantly compound (H).

$^1$H NMR (acetone-$d_6$): 5.96 (s, 0.8H, NH), 6.66-6.71 (m, 2.0H, 2×CH), 7.84 (2.1H, 2×CH), 7.93 ppm (d, J=8 Hz, 2H, 2×CH).

TLC and NMR studies indicated that the main contaminants were CL 20 (about 10% of the final product) and compound (J).

The reaction method of FIG. 2 was found to be reagent inefficient, especially the preparation of compound (E) from compound (A) and the subsequent preparation of compound (F). The final nitration product was found to contain almost 40% CL 20 as an impurity.

It was discovered that nitration of compound (B), conducted in an identical manner to the nitration used in relation to the reaction scheme of FIG. 2, gives a product which is almost entirely free of the two over-nitration products CL-20 and pentanitro-trifluoroacetyl-2,4,6,8,10,12-hexaazaisowurtzitane. This suggests that the N—COCF$_3$ group is stable under the harsh nitration conditions employed and that the COCF$_3$ group is an effective protecting group in nitration reactions. It seems likely that the CL 20 contaminant in the nitration product of compound (F) is a result of the presence of compound (E) in the crude starting material (B).

Reaction Scheme 4

(D) Synthesis of 2,6,8,10,12-penta nitro-2,4,6,8,10,12-hexa aza iso wurtzitane from 2,6,8,12-tetra acetyl-2,4,6,8,10,12-hexa aza iso wurtzitane The reaction comprises three steps:

(1) the preparation of 2,6,8,12,tetraacetyl-4-tri fluoro acetyl-2,4,6,8,10,12-hexaazaisowurtzitane (K) from 2,6,8,12-tetraacetyl-2,4,6,8,10,12-hexaazaisowurtzitane (A).

(2) Preparation of 2,6,8,10,12-pentanitro-4-trifluoro-2,4,6,8,10,12-hexaazaisowurtzitane (G) from 2,6,8,12-tetraacetyl-2,6,8,12-tetraacetyl-4-trifluoroacetyl-2,4,6,8,10, 12-hexa aza isowurtzitane (K).

(3) Preparation of 2,6,8,10,12-pentanitro-2,4,6,8,10,12-hexa azaisowurtzitane (H) from 2,6,8,10,12-pentanitro-2,4,6,8,12-trifluoroacetyl-2,4,6,8,10,12-hexaazaisowurtzitane (G).

(1) the preparation of 2,6,8,12,tetraacetyl-4-tri fluoro acetyl-2,4,6,8,10,12-hexaazaisowurtzitane from 2,6,8,12,tetraacetyl-2,4,6,8,10,12-hexaazaisowurtzitane.

Compound (A) (3.0 g) was stirred in trifluoroacetic acid (25 ml) before the addition of trifluoroacetic anhydride (10 ml). The reaction mixture was stirred at room temperature for 24 hours. The excess of trifluoroacetic acid/anhydride mixture was removed on the rotary evaporator to leave a viscous liquid. Methanol (5 ml) was added dropwise to the liquid, and then the volatile components were removed on the rotary evaporator to leave a white solid. This solid was dissolved in methanol (10 ml) and refluxed for 4.5 hours; a white solid precipitated from the solution as the reflux progressed. The methanol was then evaporated from the suspension and the resulting solid dried under vacuum at 50° C. [2.85 g, 74.0% crude yield, 292° C. melting point (DSC, ex methanol)].

NMR and IR analysis indicated that the resulting solid was compound (K).

(2) Preparation of 2,6,8,10,12-pentanitro-4-trifluoro-2,4,6,8,10,12-hexaazaisowurtzitane from 2,6,8,12-tetraacetyl-2,6,8,12-tetraacetyl-4-trifluoroacetyl-2,4,6,8,10, 12-hexaazaisowurtzitane.

A nitrating mixture was prepared by the dropwise addition of 30% SO$_3$ fuming sulphuric acid (0.4 ml) to 99.5% nitric acid (3.0 ml). The temperature was kept below 15° C. during the addition by immersion of the reaction vessel in an ice/water bath. The reaction vessel was kept in the ice/water bath during the rapid addition, with vigorous stirring, of crude compound K (500 mg). The reaction mixture was then heated at 70° C. for 3 hours (after which time TLC analysis indicated that the reaction was complete). The reaction mixture was allowed to cool before being drowned in an ice/water (100 ml) bath. The precipitate was filtered off, washed with water until the washings were neutral and dried overnight in a vacuum dessicator (390 mg, 69% yield).

TLC analysis indicated that the resulting solid was compound (G).

(3) Preparation of 2,6,8,10,12-pentanitro-2,4,6,8,10,12-hexa azaisowurtzitane from 2,6,8,10,12-pentanitro-2,4,6,8, 12-trifluoroacetyl-2,4,6,8,10,12-hexaazaisowurtzitane.

Crude compound (G) was dissolved in dry ethanol (10 ml) and stirred at room temperature for 48 hours. The solution was evaporated to dryness and the resulting yellowish solid was dried under vacuum at 50° C. for 6 hours (331 mg, 105% crude yield).

TLC and NMR analysis indicated that the solid was predominantly compound (H), with CL-20 as the main contaminant.

SYNTHESISED DERIVATIVES

The following reaction schemes demonstrate specific embodiments as to how the compounds of formula (III) may be derived from compounds of formula (I).

Reaction Scheme 5

WN$_5$H: 2,6,8,10,12-pentanitro-2,4,6,8,10,12-hexa aza iso wurtzitane.

WN$_5$A: 4-acetyl-2,6,8,10,12-pentanitro-2,4,6,8,10,12-hexa aza iso wurtzitane

Acetylation of WN5H; Formation of WN$_5$A

WN$_5$H (50 mg) was suspended in acetyl chloride (1.0 ml) and conc. sulphuric acid (two drops) was added. The reaction mixture was stirred at room temperature for 8 min, during which time the suspended material dissolved. The reaction mixture was then poured onto crushed ice (30 mg) and allowed to stand for 45 min. The precipitate was collected by filtration and washed with water until the washings were neutral, then dried overnight in a vacuum dessicator (42 mg, 76% crude yield).

IR (KBr disc): 1703.8 cm−1 (CO stretch)
$^1$H NMR (acetone-d6): 2.49 (s, 3.00H), 7.52-7.71 (m, 1.0H) and 8.03-8.33 ppm (m, 4.80H)
$^{13}$C NMR (acetone-d6): 20.49, 67.53, 71.60, 72.37, 74.88 and 169.29 ppm.

Acetylation of WN$_4$H$_2$; Formation of WN$_4$A$_2$

WN$_4$H (20 mg) was suspended in acetic anhydride (2.0 ml) and conc. sulphuric acid (1 drop) was added. All of the suspended solids immediately dissolved. The solution was stirred at room temperature for 24 h. TLC analysis at this stage indicated that no starting material remained and that a single new product (higher R$_f$) had formed. The reaction was drowned in ice/water (50 ml), the precipitate was filtered off and washed with water. Yield 21 mg (after drying).

$^1$H NMR (acetone-d6): δ 2.46 (s, 6.51H), 7.30 (m) +7.42 (m) (2.11H), 7.85 (s) +7.96 ppm (m) 4.00H).
$^{13}$C NMR (acetone-d6): 66.2, 67.5, 70.2, 71.6, 74.7, 169.8 ppm.

Reaction Scheme 6

WN$_4$H$_2$: 2,6,8,12,-tetranitro-2,4,6,8,10,12-hexa aza iso wurtzitane.

WN$_5$A: 4,10-diacetyl-2,6,8,12-tetranitro-2,4,6,8,10,12-hexa aza iso wurtzitane.

Reaction of WN$_5$H with ETNCO; Formation of WN$_5$ (CONHEt)

WN$_5$H (200 mg) anhydrous CuCl$_2$ (5-10 mg) and EtNCO (1.0 ml) were dissolved in acetonitrile (4.0 ml). The solution was heated at 55° C. for 20 h, the volatile components were rotary evaporated and the residue was transferred to a separating funnel with water (2×5 ml) and EtOAc (2×5 ml). The aqueous layer was extracted with more EtOAc (2×20 ml), the extracts were combined and washed with water, and then concentrated. rying gave a yellow solid (263 mg). A sample (20 mg) of the crude WN$_5$(CONHEt) was column purified (5 cm "Trikonex" flash tube supplied by Fisher) using 3/2 (vol)

n-heptane/EtOAc as eluent. The low $R_f$ components were recovered and re-columned (Trikonex) using 1/2 n-heptane/EtOAc.

$^1$H NMR (acetone-d6): δ 1.13 (t 3.94H), 3.28(q, 2.10 H), 6.73 (br s, 0.99H, NH), 7.67 (d, J=8.0 Hz 2.21H) 7.99 (s, 1.99H), 8.08 ppm (d, J=8.0 Hz, 2.00H)

$^{13}$C NMR (acetone-d6): 15.1, 36.8, 71.1, 71.3, 74.8 ppm.

Reaction Scheme 7

EtNCO: N-ethyl isocyanate.

$WN_5$ (CONHEt): 4-(N-ethylcarboxamido)-2,6,8,10,12-pentanitro-2,4,6,8,10,12-hexaazaisowurtzitane.

$WN_5(CONH_2)$: 4-carboxamido-2,6,8,10,12-pentanitro-2,4,6,8,10,12-hexa aza isowurtzitane Reaction of $WN_5H$ with $Cl_3CCONCO$; Formation of $WH_5$ (CONHCOCCl$_3$)

(a) $WN_5H$ (30 mg) was dissolved in acetonitrile (3.0 ml) in a nitrogen-flushed flask. The solution was stirred at 60° C. Trichloroacetyl isocyanate (0.2 ml) was added by syringe via the septum cap and stirring was continued for 4h. The volatile components were removed by rotary evaporation to give a yellow/orange, sticky solid. Trituration with first DCM and then Et$_2$O failed to cause crystallisation, the material being soluble in both solvents. The sample was dried under vacuum at 50° C. for a prolonged period. TLC analysis of the isolated material showed that all of the starting material had reacted and that a new product had been formed (possibly a single spot at low $R_f$, but badly tailed). The $^1$H NMR spectrum confirmed that the starting material was absent, and that the cage structure had been retained (all main signals below 7 ppm). There were only 3 peaks in the $^{13}$C spectrum.

$^3$H NMR (acetone-d$_6$): δ 7.50 (br s, 1.66H), 7.65 (d, J=7.7 Hz, 2.08H), 7.85 (br s, 1.19H), 8.10 (s, 1.56H), 8.19 (m, 1.51H), 8.36 ppm (s, 1.00H).

$^{13}$C NMR (acetone-d$_6$): 71.3, 71.7, 72.2, 75.0, 75.1, 150.2 ppm.

(b) $WN_5H$ (1.0 g) was dissolved in acetonitrile (10.0 ml) and stirred under $N_2$. Trichloroacetyl isocyanate (0.3 ml) was added by syringe via the septum cap. The solution was stirred at room temperature for 20 min, before the volatile components were removed by rotary evaporation. TLC analysis of the residue showed the presence of a large amount of starting material. The procedure was repeated with a further quantity of $Cl_3CCONCO$ (0.2 ml) The $^1$H NMR spectrum of the final product was virtually identical to that from the previous reaction.

Methanolysis of WN5(CONHCOCCl$_3$); Formation of $WN_5(CONH_2)$ $WN_5(CONHCOCCl_3)$ was dissolved in MeOH (10.0 ml), conc. sulphuric acid (5 drops) was added and the solution was refluxed for 2 h. The excess of solvent was removed by rotary evaporation and the residue washed into a separating funnel with water and ethyl acetate. The organic phase was removed, combined with EtOAc extracts (2×10 ml) of the aqueous portion and then washed with water (2×20 ml). The EtOAc was rotary evaporated and the remaining yellow solid was dried under vacuum (0.524 g). TLC analysis indicated that several components were present including HNIW (as an impurity from the starting material). A sample (30 mg) was purified on a Trikonex column (3/2 n-heptane/EtOAc) to remove HNIW (contaminant in WN$_5$H).

$^1$H NMR (acetone-d$_6$): δ 6.49 (br s, 1.86H, NH), 7.69 (d, J=8.0 Hz, 2.37H), 8.00 (s, 2.01H), 8.11 ppm (d J=8.0 Hz, 2.00H)

$^{13}$C NMR (acetone-d6): 70.9, 71.4, 74.8, 154.9 ppm.

Reaction Scheme 8

Cl$_3$CCONCO: N-trichloroacetyl isocyanate $WN_4(CONH_2)_2$: 4,10-bis(carboxamido)-2,6,8,12-hexaazaisowurtzitane.

WN5(CONHCOCl$_3$): 4-(N-trichloroacetyl carboxamido)-2,6,8,10,12-penta nitro-2,4,6,8,10,12-hexaazaisowurtzitane.

$WN4(CONHCOCCl_3)_2$: 4,10-bis(N-trichloroacetylcarboxamido)-2,6,8,12-tetra nitro-2,4,6,8,10,12-hexaazaisowurtzitane.

Reaction of $WN_4H_2$ with $Cl_3CCONCO$; Formation of $WN4(CONHCOCCl_3)_2$ $WN_4H_2$(400 mg) was stirred in acetonitrile (2.0 ml) under N2 and trichloroacteyl isocyanate (400 mg) was stirred in acetonitrile (2.0 ml) under $N_2$ and trichloroacetyl isocyanate (0.10 ml) was added by syringe via a septum cap. Complete dissolution occurred within approx. 3 min, but stirring was continued for a further 7 min. The volatile components were then removed by rotary evaporation to leave a yellow film. This was dried under vacuum at 50° C., during which time it crystallised to leave a very light yellow solid, 258 mg.

$^1$H NMR (acetone-d$_6$): 7.52 9s with br base, 4.00H), 7.87 (br s, 0.91H), 7.97 ppm (s, 1.75H).

$^{13}$C NMR (acetone-d$_6$): 70.6, 74.8, 92.7, 150.5, 150.6, 160.0, 160.1 ppm.

Methanolysis of $WN_4(CONHCOCCl_3)_2$; Formation of $N_4(CONH_2)_2$ $WN_4(CONHCOCCl_3)_2$ (30 mg) was dissolved in MeOH (3.0 ml), conc. sulphuric acid (2 drops) was added and the solution was refluxed for 7.5 h. The solvent was removed by rotary evaporation and water (3.0 ml) was added to the remaining thick film. The solid red precipitate which formed was filtered off. Washing with water revealed that this material was water-soluble. It was left in solution overnight then extracted with EtOAc (3×30 ml). The organic extract was combined and washed with water (2×20 ml). The extract was evaporated to dryness and dried under vacuum to leave a pale orange solid (21 mg).

NMR (acetone-d$_6$): 6.46 (br s, 3.46H, NH), 7.44 (s, 4.00H), 7.79 ppm (s, 1.92H).

Reaction Scheme 9

ClCONCO: N-chlorocarbonyl isocyanate.

$WN_5(CONHCOOEt)$: 4-(N-ethoxycarbonylcarboxamido)-2,6,8,10,12-pentanitro-2,4,6,8,10,12-hexaazaisowurtzitane.

Reaction of $WN_5H$ with (i) ClCONCO (ii) EtOH; Formation of $WN_5(CONHCOOEt)$ $WN_5H$ (50 mg) was dissolved in anhydrous acetonitrile (1.0 ml) under nitrogen. N-(chlorocarbonyl)isocyanate (0.20 ml) was added by syringe via the septum, and the solution was stirred at room temperature for 90 min. The volatile components were removed by rotary evaporation and the residue was allowed to react with EtOH (1.0 ml). The excess of EtOH was evaporated to leave a viscous liquid, which did not solidify on standing (2 h). Drying under vacuum at 60° C. finally caused solidification of some of the material; some remained as a viscous film (103 mg). A sample was purified on a Trikonex column (3/2 n-heptane/EtOAc) to remove HNIW (contaminant in WH$_5$H).

$^1$H NMR: (acetone-d$_6$): δ 1.24 (t, 12.81) 4.14 (q, 7.90H), 7.65 (d, J=8.0 Hz, 2.02H), 8.03 (s, 1.99H), 8.14 (d, J=7.9 Hz, 2.00H), 9.10 ppm (br s, 1.22H, NH).

$^{13}$C NMR (acetone-d$_6$): 14.6, 63.0, 71.4, 71.5, 75.0, 151.4, 151.9, 152.8 ppm Reaction Scheme 10

$WN_4(CONHCOOEt)_2$: 4,10-bis (N-ethoxycarbonylcarboxamido)-2,6,8,10,12-tetranitro-2,4,6,8,10,12-hexaazaisowurtzitane.

Reaction of $WN_4H_2$ with (i) ClCONCO, (ii) EtOH; Formation of WN4 (CONHCOOEt)$_2$ $WN_4H_2$ (50 mg) was suspended in anhydrous acetonitrile (1.0 ml) under $N_2$. N-(chlorocarbonyl) isocyanate (0.20 ml) was added by syringe via the septum cap. The suspension cleared almost immediately to leave a pale yellow solution which was stirred at room temperature for 10 min. The volatile components were removed by rotary evaporation to leave a viscous liquid, to which ethanol (1.0 ml) was added. An exotherm was observed, and a white precipitate formed rapidly. The excess EtOH was evaporated to leave a yellow solid. The $^1$H NMR spectrum of the material exhibited the typical hexaazaisowurtzitane methine signals in a ratio of 2:1. The presence of N-H appeared to be confirmed by FTIR.

$^1$H NMR: (acetone-$d_6$): δ 1.22 (t, 7.67H) 4.17 (q, 4.80H), 7.42 (s, 3.99H), 7.85 (s, 2.00H), 9.50 ppm (br s, 1.50H, NH).

$^{13}$C NMR (acetone-$d_6$): 14.5 62.9, 70.6, 74.8, 151.9, 152.8 ppm.

Reaction Scheme 11
WN4(NO)2: 4,10-dinitro-2,6,8,12-tetranitro-2,4,6,8,10,12-hexa aza iso wurtzitane.
Reaction of $WH_4H_2$ with $N_2O_4$; Formation of $WN_4(NO)_2$
WN4(NO)H: 4-nitroso-2,6,8,12-tetranitro-2,4,6,8,10,12-hexa aza isowurtzitane $WN_4H_2$ (25 mg) was suspended in HOAc (1.0 ml) before the addition of $N_2O_4$ (0.75 ml). The reaction mixture was stirred at room temperature for 20 h, at which point TLC showed no starting material remained. The main spot (high $R_f$) was assumed to be $WN_4(NO)_2$ and a very faint spot at lower $R_f$ was assumed to be $WN_4(NO)H$. The solid was removed by filtration. The filtrate gave no further precipitation on drowning in ice/water. The NMR spectrum of the solid confirmed that the new product was neither $WN_4(NO)H$ nor HNIW, and most probably $WN_4(NO)H$.

$^1$H NMR (acetone-d6): δ 7.96 (s, 1.00H), 8.10 (s, 2.00H), 8.22 (m, 1.14H), 8.28 (m, 1.11H), 8.54 ppm (s, 0.94H)

$^{13}$C NMR (acetone-d6): 61.6, 62.4, 73.5, 74.7, 74.9 (w), 75.2, 75.7 ppm (w).

Comparative Analysis

The comparative examples below and the synthetic routes of FIGS. 1, 2 and 3 use 2,6,8,12-tetraacetyl-2,4,6,8,10,12-hexaazaisowurtzitane (compound A) as a starting material. The production of compound A is detailed in International Patent Application WO9623792 and European Patent EP 0753519.

COMPARATIVE EXAMPLE 1

Attempts were made to nitrate 2,6,8,12-tetraacetyl-2,4,6,8,10,12-hexaazaisowurtzitane (compound A) to form 2,6,8,12-tetranitro-2,4,6,8,10,12-hexaazaisowurtzitane (compound D).

Compound A (100 mg) was dissolved in concentrated sulphuric acid (0.45 ml), and cooled to 0° C. Nitric acid (90 or 99.5 wt %, 4 or 6 equivalents) was added. The solution was maintained at 0° C. for the required period and then poured onto ice (10 g). The precipitated solid was filtered off, washed with water and dried. The product was analysed by thin layer chromatography and 1H NMR spectroscopy. TLC indicated the number of components in the product mixture and identified 2,4,6,8,10,12-hexanitro-2,4,6,8,10,12-hexaazaisowurtzitane (CL-20) when present. NMR indicated the proportion of the N-acetyl groups that remained un-nitrolysed, the content of CL-20 and the presence of NH groups. The following experimental results are representative.

Experiment 1 (using 90 wt % nitric acid, 4 equivalents, held at 0° C. for 20 hours).

The product was largely 2-acetyl-4,6,8,10,12-pentanitro-hexaazaisowurtzitane, with approx. 15% CL-20. About 22% of the N-acetyl groups remained un-nitrolysed.

Experiment 2 (using 99.5wt % nitric acid, 4 equivalents, held at 0° C. for 4 hours)

Product contained approx. 3% CL-20 with about 39% of the N-acetyl groups remained un-nitrolysed.

Experiment 3 (using 99.5wt % nitric acid, 4 equivalents, held at 0° C. for 23 hours)

Product contained approx. 56% CL-20. About 5% of the N-acetyl groups remained un-nitrolysed, the majority of this material comprised of 2-acetyl-4,6,8,10,12-pentanitro hexaazaiso wurtzitane.

There was no NMR evidence that NH groups were present. This indicates that 2,6,8,12-tetranitro-2,4,6,8,10,12-hexaisowurtzitane (compound D) was not present in the product of the reaction.

COMPARATIVE EXAMPLE 2

Attempts were made to nitrate 2,6,8,12-tetraacetyl-2,4,6,8,10,12-hexaazaisowurtzitane (compound A) to form 2,6,8,12-tetranitro-2,4,6,8,10,12-hexaazaisowurtzitane (compound D) based on the methodology of Hamilton et al. (ICT Conference on Energetic Materials, Karlsruhe, Germany, 2000, 21-1 to 21-8), varying the nitration conditions suggested by Hamilton in order to try to obtain compound (D). Compound A (175 mg) was dissolved in a cooled mixture of concentrated sulphuric acid (0.0072 ml) and 99.5 wt % nitric acid (0.50 ml) and immediately heated to 85° C. After the required period the solution was cooled and added to ice (5 g). The precipitate solid was filtered off, washed with water and dried. The product was analysed by thin layer chromatography and 1H NMR spectroscopy.

The following experimental results are representative.
Experiment 1 (held at 85° C. for 30 mins)
Product contained about 57% CL-20, with about 15% of the N-acetyl groups being un-nitrolysed.
Experiment 2 (held at 85° C. for 5 mins)
Product contained about 1% CL-20, with about 57% of the N-acetyl groups being un-nitrolysed. There was no NMR evidence that NH groups were present. This indicates that 2,6,8,12-tetranitro-2,4,6,8,1O,12-hexaazaisowurtzitane (compound D) was not present in the product of the reaction.

It has thus been shown that it has hitherto not been possible to produce 2,6,8,12-tetranitro-2,4,6,8,10,12-hexaazaiso wurtzitane (compound D) using the methods of the prior art.

The invention claimed is:
1. A method of producing a compound of formula (I)

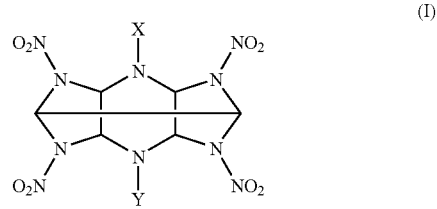

(I)

wherein
X is H, and Y is H or $NO_2$, comprising
(1) fluoroacylation of a compound of formula (II) to protect non-acylated secondary amine groups at the n-4 positions, n-10 positions or both n-4 and n-10 positions and produce a fluoroacylated compound
wherein formula (II) comprises:

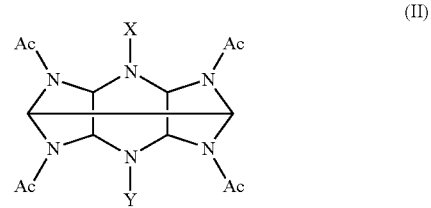

(II)

wherein X and Y are H, or
X is Ac and Y is H, and Ac is —COCH$_3$, —COCH$_2$R, where R is C$_{1-10}$ alkyl (linear or branched), —CH$_2$—C$_6$H$_5$, or C$_{1-10}$ arylalkyl;
(2) nitrolysis of the fluoroacylated compound to produce a nitrolyzed compound, and
(3) deprotection by solvolysis of the nitrolyzed compound.

2. The method of claim 1 wherein fluoroacylation is undertaken using a fluoroacylating reagent.

3. The method of claim 2 wherein the fluoroacylating reagent is a trifluoroacetylating reagent.

4. The method of claim 3 wherein the trifluoroacetylating reagent comprises trifluoroacetic anhydride, trifluoroethanoyl chloride, or a mixture of trifluoroacetic acid and trifluoroacetic anhydride.

5. The method of claim 1 wherein solvolysis comprises hydrolysis.

6. The method of claim 5 wherein solvolysis is undertaken using an alcohol or an alcohol in conjunction with a carboxylic acid salt.

7. The method of claim 1 wherein solvolysis is undertaken using sodium acetate in ethanol or sodium propionate in ethanol.

8. The method of claim 6 wherein the alcohol comprises methanol or ethanol.

9. The method of claim 1 wherein nitrolysis is undertaken using a nitrolysing reagent.

10. The method of claim 1 further comprising additional acylation prior to (1) wherein an acylating reagent is reacted with a compound of formula (II) with the proviso that X and Y are H.

11. The method of claim 10 wherein the acylating reagent is an acetylating reagent.

12. The method of claim 11 wherein the acetylating reagent comprises acetic anhydride and sodium acetate.

13. The method of claim 1 further comprising selectively deprotecting the nitrolyzed compound by solvolysis to produce a mono-amine derivative, followed by nitrolysis of the mono-amine derivative with the proviso that X and Y are H.

14. A method of making a compound of formula (III)

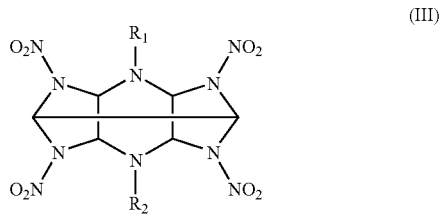

(III)

wherein
R$_1$ and R$_2$ are independently selected from:
C$_1$-C$_{10}$ alkyl, C$_1$-C$_{10}$ alkylaryl, —CH$_2$—C$_6$H$_5$,
C$_1$-C$_{10}$ polyethers, C$_1$-C$_{10}$ fluorinated polyethers, C$_1$-C$_{10}$ fluorinated alkyl, CH$_2$—C$_6$F$_5$,
COR' where R'=C$_1$-C$_{10}$ alkyl, —COCl$_3$, —COCCl$_3$,
CONHR", where R"=H, C$_1$-C$_{10}$ alkyl, —COCl$_3$, —COCCl$_3$,
CONHCO$_2$C$_2$H$_5$,
C(O)C$_m$F$_{2m}$C$_p$H$_{2p+1}$, wherein m and p are integers and are independently chosen from the range 1 to 19 and wherein m+p is less than or equal to 20, and
COCF$_3$,
comprising reacting the compound of formula (I)

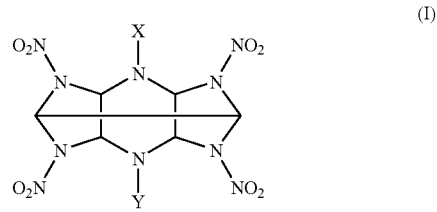

(I)

wherein
X is H, and Y is H or NO$_2$,
with an acyl halide, an acyl anhydride or an isocyanato.

15. The method of claim 14 wherein the acyl halide comprises: C$_1$-C$_{10}$ alkylacyl halides, C$_1$-C$_{10}$ alkylaryl acyl halides, CH$_2$-arylacyl halide, and R-acyl halides where R comprises
C$_1$-C$_{10}$ polyethers, C$_1$-C$_{10}$ fluorinated polyethers, C$_1$-C$_{10}$ fluorinated alkyl, CH$_2$-fluorinated phenyl,
COR', where R'=C$_1$-C$_{10}$ alkyl, COCl$_3$, COCCl$_3$,
CONHR", where R"=H, C$_1$-C$_{10}$ alkyl, COCl$_3$, COCCl$_3$,
C(O)C$_m$F$_{2m}$C$_p$H$_{2p+1}$, wherein m and p are integers and are independently chosen from the range 1 to 19 and wherein m+p is less than or equal to 20, and COCF$_3$.

16. The method of claim 14 wherein the acyl halide is an acyl chloride, an acyl bromide or an acetyl chloride.

17. The method of claim 14 wherein the acyl anhydride comprises
C$_1$-C$_{10}$ alkylacylanhydride, C$_1$-C$_{10}$ alkylarylacylanhydride, CH$_2$-arylacylanhydride, and R-acylanhydrides where R comprises C$_1$-C$_{10}$ polyethers, C$_1$-C$_{10}$ fluorinated polyethers, C$_1$-C$_{10}$ fluorinated alkyl, CH$_2$-fluorinated phenyl, as well as R acyl anhydrides where R comprises:
COR', where R'=C$_1$-C$_{10}$ alkyl, COCl$_3$, COCCl$_3$,
CONHR", where R"=H, C$_1$-C$_{10}$ alkyl, COCl$_3$, COCCl$_3$,
C(O)C$_m$F$_{2m}$C$_p$H$_{2p+1}$, wherein m and p are integers and are independently chosen from the range 1 to 19 and wherein m+p is less than or equal to 20, and COCF$_3$.

18. The method of claim 14 wherein the acyl anhydride comprises acetic anhydride.

19. The method of claim 14 wherein the isocyanate comprises N-(chlororcarbonyl)isocyanate or trichloroacetyl isocyanate.

20. The method of claim 14 wherein the compound of formula (I) is reacted with an isocyanate to form a product that is reacted with an alcohol.

21. The method of claim 20 wherein the alcohol is methanol.

* * * * *